United States Patent [19]

Lin

[11] Patent Number: 5,685,094
[45] Date of Patent: Nov. 11, 1997

[54] VENTILATED MASSAGING INSOLE

[76] Inventor: John H. J. Lin, No. 8, Jing-Cherng 11 Street, Taichung City, Taiwan

[21] Appl. No.: 635,522

[22] Filed: Apr. 22, 1996

[51] Int. Cl.[6] .................................................. A61F 5/14
[52] U.S. Cl. ................................................. 36/141; 36/43
[58] Field of Search ............................. 36/140, 141, 11.5, 36/43, 44, 3 B

[56] References Cited

U.S. PATENT DOCUMENTS

| | | | |
|---|---|---|---|
| 4,033,054 | 7/1977 | Fukuoka | 36/141 X |
| 4,831,749 | 5/1989 | Tsai | 36/141 X |
| 5,322,056 | 6/1994 | Menghi et al. | 36/11.5 X |
| 5,551,173 | 9/1996 | Chambers | 36/141 X |
| 5,553,398 | 9/1996 | Schnewlin-Maier | 36/141 X |

*Primary Examiner*—B. Bayoan
*Attorney, Agent, or Firm*—Morton J. Rosenberg; David I. Klein

[57] ABSTRACT

An insole has a configuration corresponding to either one of human feet, the insole having five toe recesses defined therein near a front end of the insole, each one of the toe recesses having a first boss extending from a bottom defining the toe recess, a first arch protrusion extending from the insole near the toe recesses and a central protrusion extending from a mediate portion of the insole, a rear end plan area defined near a rear end of the insole and a side protrusion extending from an inner side of the insole, each of the first arch protrusion and the central protrusion having at least one magnetic element received therein, the plan area having a protrusion extending therefrom in which a third recess is defined for an other magnetic element being received therein, a fourth recess defined in the insole near an outer side of the insole and yet another magnetic element being received in the fourth recess, the insole having a plurality of tiny bosses extending upwardly from the rest area of the insole and a plurality of tiny holes defined in the same area, and the insole having a plurality of support rods extending from an under side thereof.

1 Claim, 2 Drawing Sheets

VENTILATED MASSAGING INSOLE

BACKGROUND OF THE INVENTION

1. Field of the Invention

The present invention relates to an insole and more particularly to an insole having a plurality of protrusions extending from an upper side thereof and having a plurality of holes defined therein, and having magnetic elements disposed in suitable positions in said upper side of the insole.

2. Brief Description of the Prior Art

Conventional insoles are made of felt, rubber-foam even straw and cork, all the insoles are a flat sheet with a configuration of human foot and are design to provide a satisfactory wearing when wearing shoes. However, the sole of the human foot is not exactly a flat fashion, the flat insole in fact cannot provide a well support to the foot. Furthermore, the under side of the insole is flat and is laid on the flat inner bottom of the shoe such that the air existed between the sole of foot and the insole and between the inner bottom of the shoe and the under side of the insole lacks a sufficient communication with fresh air, thus an unsatisfactory odor may be produced.

The present invention intends to provide an improved insole which has suitable protrusions extending upwardly from an upper side thereof, support rods extending from an under side thereof, a plurality of holes defined in the insole and magnetic elements received in recesses defined in the upper side of the insole to mitigate and/or obviate the above-mentioned problems.

SUMMARY OF THE INVENTION

The present invention provides an insole which has a configuration corresponding to either one of human feet, the insole having five toe recesses defined in the upper side near the front end, each of the toe recesses having a first boss extending from a bottom defining the toe recess. A first arch protrusion transversely extends from the upper side and is located at a position having a distance measured from the first arch to the front end longer than a distance measured from the toe recesses to the front end. The first arch has a first recess defined therein for a first magnetic element received therein. A plurality of first holes are defined in the first arch protrusion.

A central protrusion extends from a mediate portion on a longitudinal axis of the insole, the central protrusion having three second recesses defined longitudinally therein each for a second magnetic element received therein. The central protrusion has a plurality of second bosses extending upwardly therefrom and has a plurality of second holes defined therein.

A rear end plane area is defined near the rear end of the insole and has a protrusion extending upwardly therefrom in which a third recess is defined. A third magnetic element is received in the third recess.

A fourth recess is defined in the insole between the central protrusion and the rear end plan area and is located near an outer side of the insole, a fourth magnetic element being received in the fourth recess.

The insole has a side protrusion extending upwardly from an inner side thereof, the side protrusion having a plurality of third bosses extending upwardly therefrom and having a plurality of third holes defined therein.

A plurality of tiny holes are defined in the rest area of the insole and a plurality of tiny bosses extend upwardly from the same area of the upper side of the insole.

It is an object of the present invention to provide an insole having suitable protrusions extending therefrom and each of the protrusions having a magnetic element disposed thereto.

It is another object of the present invention to provide an insole having support rods extending from an under side thereof.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
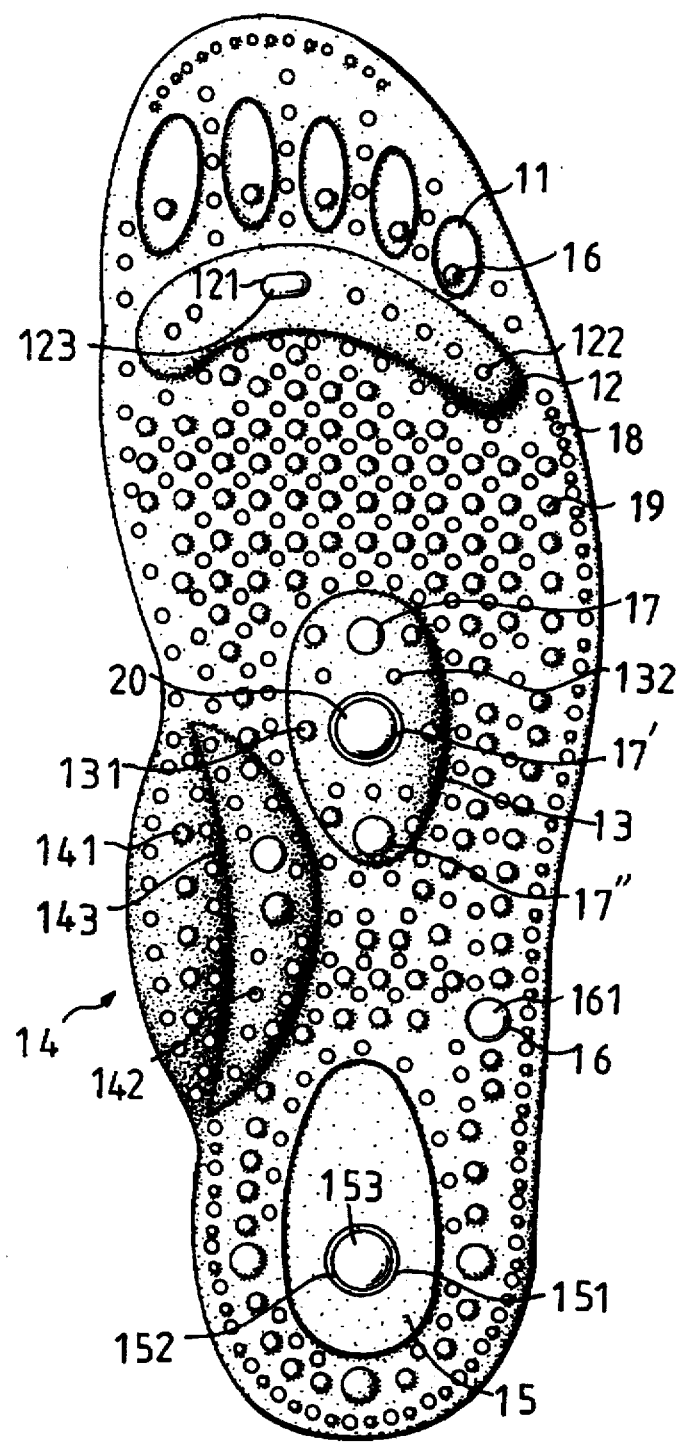
FIG. 1 is a top plan view of an insole in accordance with the present invention.
Figure 2:
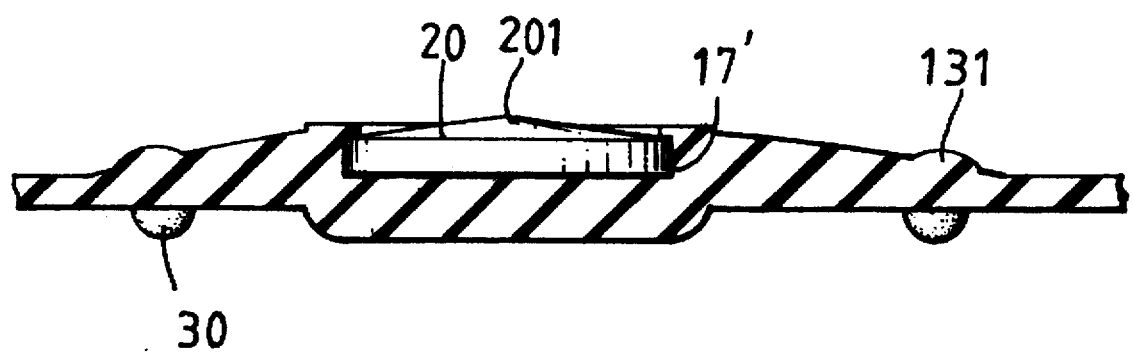
FIG. 2 is an end plan view, partly in section, of the insole to show a magnetic element received in a recess defined in the insole.

Referring to FIGS. 1 and 2, an insole in accordance with the present invention having a configuration corresponding to either one of human feet (not shown), the insole comprising an upper side, an under side, a front end and a rear end, five toe recesses 11 defined in the upper side near the front end, each of the toe recesses 11 having a first boss 16 extending from a bottom defining the toe recess 11. A first arch protrusion 12 transversely extends from the upper side and is located at a position having a distance, measured from the first arch protrusion 12 to the front end, longer than a distance measured from the toe recesses 11 to the front end. The first arch protrusion 12 has a first recess 121 and a plurality of first holes 122 defined therein. A first magnetic element 123 is received in the first recess 121.

A central protrusion 13 being an egg-like configuration extends from a mediate portion and is located on a longitudinal axis of the insole. The central protrusion 13 has three second recesses 17, 17', 17" respectively defined longitudinally therein. Each one of the three second recesses 17, 17', 17" has a second magnetic element 20 received therein. The central protrusion 13 further has a plurality of second bosses 131 extending upwardly therefrom and has a plurality of second holes 132 defined therein.

A rear end plan area 15 is defined near the rear end of the insole and has a protrusion 151 extending upwardly therefrom in which a third recess 152 is defined. A third magnetic element 153 is received in the third recess 152.

A fourth recess 16 is defined in the insole between the central protrusion 13 and the rear end plan area and is located near an outer side of the insole, a fourth magnetic 161 element being received in the fourth recess 16.

The insole has a side protrusion 14 extending upwardly from an inner side thereof, the side protrusion 14 having a plurality of third bosses 141 extending upwardly therefrom and having a plurality of third holes 142 defined therein. The side protrusion 14 has a curved groove 143 defined longitudinally therein to divide the side protrusion 14 into two portions.

A plurality of tiny holes 18 are defined in the rest of the insole area and a plurality of tiny bosses 19 extend upwardly from the same area as having the tiny holes 18 of the upper side of the insole.

Each of the first magnetic element 123, the second magnetic elements 20, the third magnetic element 153 and the fourth magnetic element 161 has a cone-shaped portion 201 extending upwardly from a center thereof.

The insole has a plurality of support rods 30 extending from an under side thereof so as to defined a space between an inner bottom of a shoe (not shown) and the under side of the insole.

Accordingly, the insole provides a satisfactory engagement between the insole and a sole of the foot (not shown) put on the insole, all the kinds of protrusions 12, 13, 14 fill the concave portions of the foot when the foot stands on the insole. Furthermore, the magnetic elements 123, 20, 161, 153 communicate to a magnetic field of human body and the space defined between the inner bottom of the shoe (not shown) and the insole and the holes defined in the insole provide good ventilation for the foot.

Although the invention has been explained in relation to its preferred embodiment, it is to be understood that many other possible modifications and variations can be made without departing from the spirit and scope of the invention as hereinafter claimed.

What is claimed is:

1. An insole having a configuration corresponding to a human foot, said insole having opposing upper and bottom sides, a front end and a longitudinally displaced rear end, said insole comprising:

five toe receiving recesses formed in said upper side adjacent said front end, each of said five toe receiving recesses having a singular first boss extending from a bottom surface of said recess;

an arch shaped protrusion projecting from said upper side and extending in a direction transverse said longitudinal direction, said arch shaped protrusion being longitudinally spaced from said five toe receiving recesses, said arch shaped protrusion having a first recess formed therein and a plurality of first holes formed therethrough in open communication with said bottom side;

a first magnetic element disposed in said first recess for contact with a user's foot;

a central protrusion projecting from said upper side intermediate said front and rear ends, said central protrusion having a plurality of second recesses formed therein and a plurality of second holes formed therethrough in open communication with said bottom side, said central protrusion having a plurality of second bosses extending upwardly therefrom;

a plurality of second magnetic elements respectively disposed in said plurality of second recesses for contact with the user's foot;

a rear end plan area disposed adjacent said rear end, said rear end plan area having protrusion extending upwardly therefrom and a third recess formed in said protrusion of said rear end plan area;

a third magnetic element disposed in said third recess for contact with the user's foot;

a side protrusion extending upwardly from an inner side of said insole, said side protrusion having a plurality of third bosses extending upwardly therefrom and a plurality of third holes formed therethrough in open communication with said bottom side;

said insole having a fourth recess formed in said upper side longitudinally disposed intermediate said central protrusion and said rear end plan area and located on a side of said insole opposite said side protrusion;

a fourth magnetic element disposed in said fourth recess for contact with the user's foot;

a remaining area of said insole having a plurality of small bosses extending upwardly from said upper side and a plurality of small holes formed therethrough in open communication with said bottom side; and a plurality of support rods extending downwardly from said bottom side for forming an air space below said bottom side to provide ventilation of the user's foot through said plurality of first holes, said plurality of second holes, said plurality of third holes, and said plurality of small holes.

* * * * *